(12) United States Patent
Takano et al.

(10) Patent No.: US 7,439,357 B2
(45) Date of Patent: Oct. 21, 2008

(54) PROCESS FOR PREPARING THIAZOLE BY AMINOMETHYLATION

(75) Inventors: Naoyuki Takano, Ibaraki-shi (JP); Shinzo Seko, Oita (JP); Kazuyuki Tanaka, Oita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 11/629,754

(22) PCT Filed: Jun. 10, 2005

(86) PCT No.: PCT/JP2005/011095

§ 371 (c)(1),
(2), (4) Date: Dec. 15, 2006

(87) PCT Pub. No.: WO2005/123704

PCT Pub. Date: Dec. 29, 2005

(65) Prior Publication Data

US 2007/0197803 A1    Aug. 23, 2007

(30) Foreign Application Priority Data

Jun. 17, 2004  (JP) .............................. 2004-179472
Apr. 7, 2005   (JP) .............................. 2005-110701

(51) Int. Cl.
*C07D 251/04*   (2006.01)
*C07D 277/28*   (2006.01)

(52) U.S. Cl. ..................... 544/193; 548/198

(58) Field of Classification Search ................. 544/193; 548/198

See application file for complete search history.

(56) References Cited

U.S. PATENT DOCUMENTS

| 5,180,833 A | 1/1993 | Uneme et al. |
| 5,849,768 A | 12/1998 | Minamida et al. |
| 6,403,803 B1 | 6/2002 | Rauchschwalbe |

FOREIGN PATENT DOCUMENTS

| JP | 4-21674 | 1/1992 |
| JP | 5-286936 | 11/1993 |
| JP | 2000-143648 | 5/2000 |
| RU | 798102 | 1/1981 |
| WO | 00/21943 | 4/2000 |

OTHER PUBLICATIONS

Patent Abstracts of Japan, vol. 2000, No. 08 Oct. 6, 2000 & JP 2000 143648 A (Takeda Chem. Ind. Ltd.), May 26, 2000.

Patent Abstracts of Japan, vol. 018, No. 075 (C-1163), Feb. 8, 1994 & JP 05 286936 A (Takeda Chem. Ind. Ltd.), Nov. 2, 1993.

Patent Abstracts of Japan, vol. 016, No. 180 (C-0935), Apr. 30, 1992 & JP 04 021674 A (Nippon Soda Co., Ltd.), Jan. 24, 1992.

Patent Abstracts of Japan, vol. 016, No. 581 (C-1012), Dec. 21, 1992 & JP 04 234864 A (Takeda Chem. Ind. Ltd.), Aug. 24, 1992.

Howard D. Hartough et al., "Aminomethylation of Thiophene. II. The Intermediate N-(2-Thenyl)-formaldimines and their Reactions", J. Amer. Chem. Soc., vol. 70, pp. 4013-4017, XP002339183, 1948.

John Graymore, "The Preparation of Benzylamines from Benzyl Halides and Hexamethylenetetramine", J. Chem. Soc., pp. 1116-1118, 1947.

*Primary Examiner*—Venkataraman Balasubramanian
(74) *Attorney, Agent, or Firm*—Wenderoth, Lind & Ponack, L.L.P.

(57) ABSTRACT

A process for preparing a thiazole compound of formula (3): wherein $X^1$ represents a hydrogen atom or a halogen atom comprising reacting a compound of formula (1): wherein $X^1$ is as defined above, and $X^2$ represents a halogen atom, with ammonia and formaldehyde to obtain a hexahydrotriazine compound of formula (2): wherein $X^1$ is as defined above, and hydrolyzing the compound of formula (2).

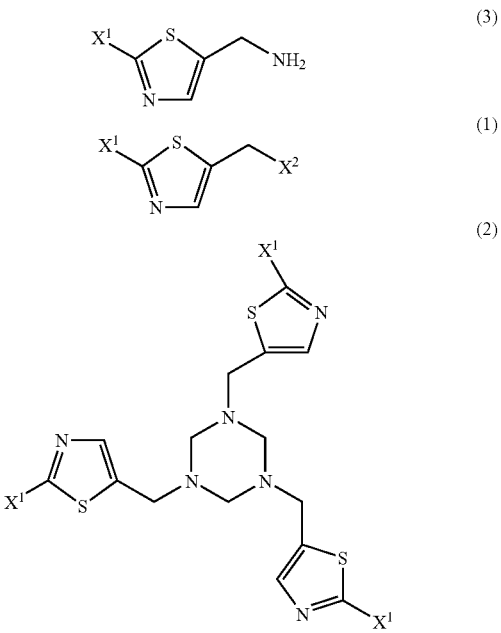

13 Claims, No Drawings

PROCESS FOR PREPARING THIAZOLE BY AMINOMETHYLATION

TECHNICAL FIELD

The present invention relates to a process for preparing a thiazole compound.

BACKGROUND ART

A thiazole compound, typically, 2-chloro-5-(aminomethyl)thiazole, of formula (3):

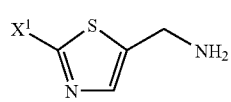
(3)

wherein $X^1$ represents a hydrogen atom or a halogen atom, is a useful compound as an intermediate for pharmaceuticals and agrochemicals (see, e.g., JP 7-14916 B). For preparing the thiazole compound, several processes have been known. For example, (a) a compound of formula (1):

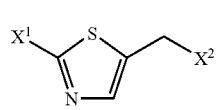
(1)

wherein $X^1$ is as defined above, and $X^2$ represents a halogen atom, is reacted with hexamethylenetetramine, followed by hydrolysis (see, e.g., JP 4-234864 A and JP 4-21674 A); (b) the compound of formula (1) is reacted with potassium phthalimide, followed by hydrazinolysis (see, e.g., JP 4-234864 A); (c) the compound of formula (1) is reacted with formamide, followed by hydrolysis (see, e.g., JP 5-286936 A); and (d) the compound of formula (1) is reacted with ammonia (see, e.g., JP 4-234864 A and JP 2000-143648 A).

However, the above processes (a) to (c) are not necessarily satisfactory from an industrial point of view because yields of the target thiazole compound of formula (3) are low in these processes. Although the above process (d) has an advantage over the processes (a) to (c) because of the use of low-priced ammonia, a considerable amount of a by-product compound of formula (4):

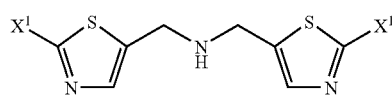
(4)

wherein $X^1$ is as defined above, is formed even when using ammonia in 20 mol-fold amount or more relative to the compound of formula (1), which results in a low yield of the target thiazole compound of formula (3). Therefore, further improvement has been desired.

DISCLOSURE OF INVENTION

Under these circumstances, the present inventors have studied intensively to develop an industrially advantageous process for preparing the thiazole compound of formula (3) using low-priced ammonia with suppressing the formation of the by-product, i.e., the compound of formula (4), and have found that the target thiazole compound of formula (3) can be prepared with suppressing the formation of the by-product, the compound of formula (4), by reacting the compound of formula (1) with ammonia and formaldehyde, which is also low-priced and readily available, to obtain a hexahydrotriazine compound, which is a novel compound, of formula (2):

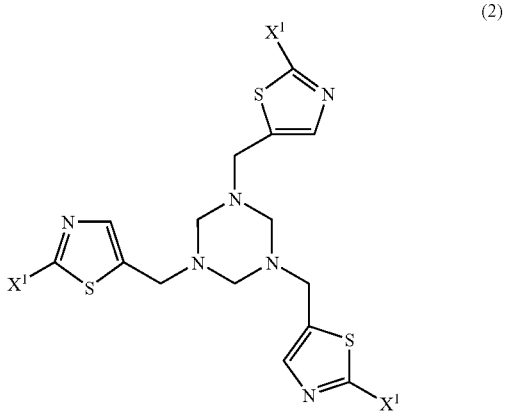
(2)

wherein $X^1$ is as defined above, and then hydrolyzing the hexahydrotriazine compound of formula (2). Thus, the present invention have been completed.

That is, the present invention provides a process for preparing a thiazole compound of formula (3):

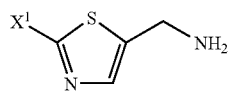
(3)

wherein $X^1$ is as defined above, which comprises the steps of:

reacting a compound of formula (1):

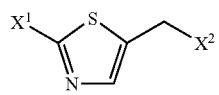
(1)

wherein $X^1$ represents a hydrogen atom, or a halogen atom, and $X^2$ represents a halogen atom, with ammonia and formaldehyde to obtain a hexahydrotriazine compound of formula (2):

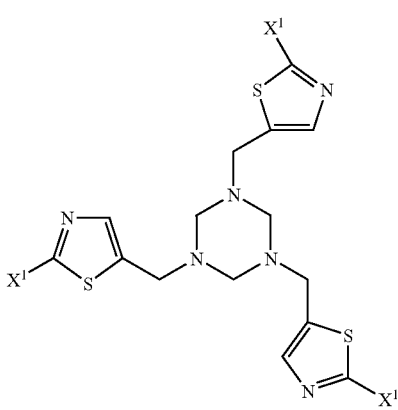

wherein $X^1$ is as defined above, and hydrolyzing the resulting hexahydrotriazine compound of formula (2).

BEST MODE FOR CARRYING OUT THE INVENTION

First, the step for reacting a compound of formula (1):

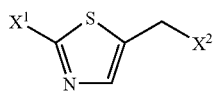

wherein $X^1$ represents a hydrogen atom or a halogen atom, and $X^2$ represents a halogen atom (hereinafter, abbreviated as compound (1)), with ammonia and formaldehyde to obtain a hexahydrotriazine compound of formula (2):

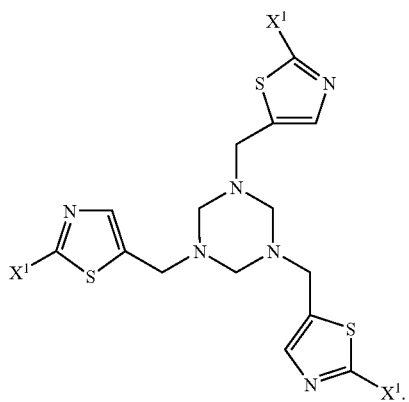

wherein $X^1$ is as defined above (hereinafter, abbreviated as hexahydrotriazine compound (2)), will be explained.

In compound (1), $X^1$ represents a hydrogen atom or a halogen atom, and X represents a halogen atom. Examples of the halogen atom include a chlorine atom, a bromine atom, an iodine atom, and the like.

Examples of compound (1) include, for example, 5-(chloromethyl)thiazole, 2-chloro-5-(chloromethyl)thiazole, 2-chloro-5-(bromomethyl)thiazole, 2-bromo-5-(bromomethyl)thiazole, 2-chloro-5-(iodomethyl)thiazole, 2-bromo-5-(iodomethyl)thiazole, 2-iodo-5-(iodomethyl)thiazole, and the like.

Compound (1) can be prepared according to a known method, for example, the method described in JP 4-234864 A.

Compound (1) may be in the free form, or may be in an acid addition salt form. Examples of the acid of acid addition salt include inorganic acids such as hydrochloric acid, hydrobromic acid, sulfuric acid, perchloric acid, and the like; and organic acids such as acetic acid, methanesulfonic acid, trifluoromethanesulfonic acid, p-toluenesulfonic acid, and the like.

As ammonia, ammonia gas may be used, or liquid ammonia may be used. Further, ammonia water may be used, or a solution of ammonia in an organic solvent that can solubilize ammonia such as methanol may be used. From a viewpoint of ease of handling and yield, a solution of ammonia in an organic solvent is preferably used.

Ammonia is usually used in the amount of 1 to 30 moles, preferably 2 to 15 moles, and more preferably 2 to 10 moles per mol of compound (1). In case of using compound (1) in the form of an acid addition salt, the amount of ammonia that may be used can be determined by taking the acid in acid addition salt into consideration.

As formaldehyde, formaldehyde gas may be used, but from a viewpoint of handling, paraformaldehyde or formalin is preferably used, and paraformaldehyde is more preferably used. Formaldehyde is usually used in the amount of 1 to 10 moles, preferably 1 to 8 moles, and more preferably 1 to 5 moles per mol of compound (1). Further, preferably, the amount of formaldehyde that may be used per mol of compound (1) is smaller than that of ammonia.

The reaction temperature is usually 15 to 100° C., preferably 20 to 90° C. The reaction is usually carried out at atmospheric pressure or under pressure of not higher than 0.5 MPa (gauge pressure).

The reaction may be carried out with no solvent, but preferably carried out in an inert solvent. Examples of the solvent include, for example, alcohols such as methanol, ethanol, n-propanol, isopropanol, and the like; aromatic hydrocarbons such as toluene, xylene, and the like; halogenated hydrocarbons such as chlorobenzene, dichlorobenzene, and the like; aliphatic hydrocarbons such as hexane, heptane, cyclohexane, and the like; ethers such as diethyl ether, tetrahydrofuran, dioxane, and the like; aprotic polar solvents such as acetonitrile, propionitrile, dimethylsulfoxide, N,N-dimethyl acetamide, and the like; and water. They can be used alone or as a mixture of the solvents. Alcohols and water are preferable, and alcohols are more preferable. The amount of the solvent that may be used is usually 1 to 10 parts by weight per part by weight of compound (1).

The reaction is usually carried out by mixing and bringing compound (1) into contact with ammonia and formaldehyde, and the order of mixing thereof is not specifically limited. For example, compound (1) may be mixed with ammonia and formaldehyde to carry out the reaction at a given temperature, or compound (1) mixed in advance with formaldehyde may be added to ammonia to carry out the reaction. Alternatively, ammonia and formaldehyde may be mixed and to this mixture is added compound (1) to carry out the reaction. Further, to formaldehyde may be added compound (1) and ammonia simultaneously to carry out the reaction. Furthermore, to ammonia may be added compound (1) and formaldehyde simultaneously to carry out the reaction.

If necessary, the reaction may be carried out in the presence of a quaternary ammonium salt such as triethylbenzylammonium chloride, tri-n-octylmethylammonium chloride, trimethyldecylammonium chloride, tetramethylammonium bromide, tetra-n-butylammonium bromide, or the like; or a phase transfer catalyst such as crown ether, or the like.

It is considered that, by this reaction, a methyleneimine compound which is an unstable intermediate, and of formula (5):

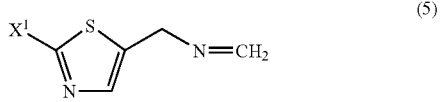

wherein $X^1$ is as defined above, is formed, followed by trimerization thereof to form hexahydrotriazine compound (2).

After completion of the reaction, a reaction mixture containing hexahydrotriazine compound (2) is obtained, and hexahydrotriazine compound (2) can be isolated by, for example, concentrating the reaction mixture. Alternatively, hexahydrotriazine compound (2) can be isolated as crystals by cooling the reaction mixture as it is or after partial concentration. Further, hexahydrotriazine compound (2) can be isolated by adding water and a hydrophobic organic solvent to the reaction mixture as it is or after concentration thereof to subject the mixture to extraction treatment, and concentrating the resulting organic layer. Furthermore, hexahydrotriazine compound (2) can be isolated as an acid addition salt such as its hydrochloride, sulfate, or the like.

Examples of the hydrophobic organic solvent include halogenated hydrocarbons such as chlorobenzene, dichlorobenzene, and the like; esters such as ethyl acetate, butyl acetate, and the like; ketones such as methyl ethyl ketone, methyl isobutyl ketone, and the like; and aromatic hydrocarbons such as toluene, xylene, and the like. They can be used alone or as a mixture of the solvents. The amount thereof that may be used is not specifically limited.

Alternatively, without isolating hexahydrotriazine compound (2) from the reaction mixture, the reaction mixture or an organic layer containing hexahydrotriazine compound (2) may be used in the subsequent hydrolyzing step described hereinafter.

Examples of hexahydrotriazine compound (2) thus obtained include, for example, 1,3,5-tris{(thiazol-5-yl)methyl}-1,3,5-hexahydrotriazine, 1,3,5-tris{(2-chlorothiazol-5-yl)methyl}-1,3,5-hexahydrotriazine, 1,3,5-tris{(2-bromothiazol-5-yl)methyl}-1,3,5-hexahydrotriazine, and the like.

Next, the step for preparing the thiazole compound of formula (3):

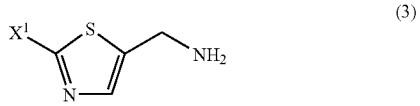

wherein $X^1$ is as defined above (hereinafter, abbreviated as thiazole compound (3)), by hydrolyzing hexahydrotriazine compound (2) obtained will be explained.

This step is hydrolysis of hexahydrotriazine compound (2) obtained in the previous step to convert it into thiazole compound (3), and usually carried out by mixing hexahydrotriazine compound (2) and an aqueous solution of an acid to allow to come into contact with each other. Examples of the aqueous solution of an acid include, for example, an aqueous solution of hydrochloric acid, sulfuric acid, phosphoric acid, nitric acid, or the like. An aqueous solution of hydrochloric acid or sulfuric acid is preferable. The concentration of the acid in the aqueous solution is not specifically limited. The acid is usually used in the amount of 1 to 30 moles, preferably 3 to 15 moles per mol of hexahydrotriazine compound (2).

As described above, hexahydrotriazine compound (2) formed in the previous step may be isolated from the reaction mixture, and then hydrolyzed, or the reaction mixture or an organic layer containing hexahydrotriazine compound (2) may be subjected directly to the hydrolysis without isolating hexahydrotriazine compound (2).

The temperature for hydrolysis is usually 10 to 100° C., preferably 25 to 70° C.

As hydrolysis of hexahydrotriazine compound (2) proceeds, formaldehyde is formed as a by-product. In order to facilitate removal of the by-product, formaldehyde, the hydrolysis of hexahydrotriazine compound (2) is preferably carried out in the presence of a lower alcohol compound to convert formaldehyde formed as the by-product into acetal. Examples of the lower alcohol compound include, for example, lower alcohol compounds having 1 to 4 carbon atoms such as methanol, ethanol, and the like. The lower alcohol compound is usually used in the amount of not less than 1.5 moles, preferably not less than 2 moles, more preferably not less than 2.5 moles per mol of hexahydrotriazine compound (2), and the upper limit is not specifically limited. When the reaction mixture containing hexahydrotriazine compound (2) is used as it is, and when the lower alcohol compound is present in the reaction mixture, the amount of the lower alcohol compound that may be used may be determined by taking the amount thereof in the reaction mixture into consideration. Further, sometimes, formaldehyde remains in the reaction mixture. In such a case, the lower alcohol compound may be used in an amount sufficient to convert not only formaldehyde formed as the by-product but also formaldehyde remained in the reaction mixture into acetal. Of course, after the hydrolysis of hexahydrotriazine compound (2), formaldehyde may be converted into acetal.

After completion of the hydrolysis, thiazole compound (3) or an acid addition salt thereof can be isolated by, for example, concentration. Alternatively, thiazole compound (3) can be isolated by concentrating the reaction mixture, adding an aqueous solution of an alkali and a hydrophobic organic solvent thereto to subject the mixture to extraction treatment, and concentrating the resulting organic layer. Examples of the aqueous solution of an alkali include an aqueous solution of an alkali metal hydroxide such as an aqueous sodium hydroxide solution, or the like. The amount of the aqueous solution of an alkali that may be used is such that pH of the aqueous layer upon extraction is within the range of usually 8 to 14, preferably 10 to 14.

Further, an acid addition salt of thiazole compound (3) can be isolated by mixing the organic layer obtained in the above extraction with an aqueous solution of an acid, separating into layers to obtain an aqueous solution containing an acid addition salt of thiazole compound (3) and, optionally, partially concentrating the aqueous solution. Further, crystals of an acid addition salt of thiazole compound (3) can be precipitate by adding an insufficient solvent scarcely dissolving the acid addition salt of thiazole compound (3) to the above aqueous solution. Examples of the aqueous solution of an acid include an aqueous solution of an acid such as hydrochloric acid, sulfuric acid, acetic acid, methanesulfonic acid, or the like.

The amount of the aqueous solution that may be used is such that pH of the aqueous layer upon extraction is within the range of usually 2.5 to 5.5, preferably 3 to 5. If the aqueous solution containing the acid addition salt of thiazole compound (3) thus obtained is colored, the solution may be subjected to decolorization treatment by, for example, adding a decoloring agent such as activated charcoal to the aqueous solution.

Examples of thiazole compound (3) thus obtained include 5-(aminomethyl)thiazole, 2-chloro-5-(aminomethyl)thiazole, 2-bromo-5-(aminomethyl)thiazole, and the like.

The present invention will be further illustrated in detail by the following Examples but the present invention is not limited to these Examples. For the analyses in Examples, high performance liquid chromatography (HPLC) was used; and a yield and a recovery were calculated on the basis of 2-chloro-5-(chloromethyl)thiazole. In the following Examples, all the parts and percents are by weight unless otherwise stated.

EXAMPLE 1

To a glass autoclave, 95.3 parts of 2-chloro-5-(chloromethyl)thiazole (content: 96.5%), 51.9 parts of paraformaldehyde (content: 95%) and 311 parts of a 12% ammonia solution in methanol were charged, and the mixture was reacted with stirring at an inner temperature of 70° C. for 3 hours. The maximum inner pressure (gauge pressure) during the reaction was 0.09 MPa. The reaction mixture containing 1,3,5-tris{(2-chlorothiazol-5-yl)methyl}-1,3,5-hexahydrotriazine thus obtained was transferred into a four-neck flask by washing the autoclave with 150 parts of methanol, bubbled with nitrogen for 15 minutes to expel ammonium remaining in the reaction mixture, and then concentrated under reduced pressure to distill off 60 parts of methanol. To the resultant concentrated residue were added 60 parts of methanol and 188 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 246 parts of a concentrated residue. To the concentrated residue were added 57.5 parts of water, 282 parts of methyl isobutyl ketone and 367 parts of an aqueous 27% sodium hydroxide solution to adjust to pH 13, thereby subjecting the mixture to extraction treatment, and obtaining an organic layer and an aqueous layer. The aqueous layer was further extracted three times with methyl isobutyl ketone, and the methyl isobutyl ketone layers obtained were combined with the previously obtained organic layer to obtain a solution containing 2-chloro-5-(aminomethyl)thiazole. The yield of 2-chloro-5-(aminomethyl)thiazole was 91.2%, and the yield of bis{(2-chlorothiazol-5-yl)methyl}amine was 2.8%.

The solution containing 2-chloro-5-(aminomethyl)thiazole thus obtained was washed with 33.6 parts of an aqueous 14% sodium hydroxide solution, followed by addition of 100 parts of water and 55.7 parts of 35% hydrochloric acid to adjust to pH 3.3. Then, the layers were separated, and 230 parts of the resultant aqueous layer was concentrated under reduced pressure to obtain 194 parts of a concentrated residue. To the concentrated residue was added 1 part of activated charcoal and the mixture was maintained with stirring at room temperature for 1 hour. The activated charcoal was filtered and washed with about 10 parts of water to obtain 204 parts of an aqueous solution containing 2-chloro-5-(aminomethyl)thiazole hydrochloride. The content of 2-chloro-5-(aminomethyl)thiazole hydrochloride was 42.4% and the yield was 85.2%.

EXAMPLE 2

To a glass autoclave, 16.7 parts of 2-chloro-5-(chloromethyl)thiazole (content: 95.7%), 9.04 parts of paraformaldehyde (content: 95%) and 16.7 parts of methanol were charged, and adjusted to an inner temperature of 70° C. To this was added dropwise 57.9 parts by weight of a 14% ammonia solution in methanol over 1 hour. After completion of addition, the mixture was reacted at the same temperature for 3 hours. The maximum inner pressure (gauge pressure) during the reaction was 0.15 MPa. The reaction mixture containing 1,3,5-tris{(2-chlorothiazol-5-yl)methyl}-1,3,5-hexahydrotriazine obtained was transferred into a four-neck flask by washing the autoclave with 50 parts of methanol, and concentrated under reduced pressure to obtain 42.7 parts of a concentrated residue. To the concentrated residue was added 73.2 parts of methanol and 32.8 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 42.2 parts of a concentrated residue. To the concentrated residue were added 49 parts of methyl isobutyl ketone and 69 parts of an aqueous 27% sodium hydroxide solution to adjust to pH 13, thereby subjecting the mixture to extraction treatment, and obtaining an organic layer and an aqueous layer. The aqueous layer was further extracted three times with methyl isobutyl ketone, and the methyl isobutyl ketone layers obtained were combined with the previously obtained organic layer to obtain a solution containing 2-chloro-5-(aminomethyl)thiazole. The yield of 2-chloro-5-(aminomethyl)thiazole was 87.1%, and the yield of bis{(2-chlorothiazol-5-yl)methyl}amine was 1.2%.

EXAMPLE 3

To a glass autoclave, 16.8 parts of 2-chloro-5-(chloromethyl)thiazole (content: 95.6%), 9.05 parts of paraformaldehyde (content: 95%) and 135 parts of a 24% ammonia solution in methanol were charged, and the mixture was reacted with stirring at an inner temperature of 70° C. for 3 hours. The maximum inner pressure (gauge pressure) during the reaction was 0.37 MPa. The reaction mixture containing 1,3,5-tris{(2-chlorothiazol-5-yl)methyl}-1,3,5-hexahydrotriazine obtained was transferred into a four-neck flask by washing the autoclave with 20 parts of methanol, and concentrated under reduced pressure to obtain 40 parts by a concentrated residue. To the concentrated residue were added 73.2 parts of methanol and 32.8 parts of 35% hydrochloric acid, and refluxed at an inner temperature of about 60° C. for 1.5 hours. The mixture was cooled to an inner temperature of not higher than 40° C., and then concentrated under reduced pressure to obtain 41.7 parts of a concentrated residue. To the concentrated residue were added 49 parts of toluene and 51.8 parts of an aqueous 30% sodium hydroxide solution to adjust to pH 13, thereby subjecting the mixture to extraction treatment and obtaining an organic layer and an aqueous layer. The aqueous layer was further extracted three times with toluene, and the toluene layers obtained were combined with the previously obtained organic layer to obtain a solution containing 2-chloro-5-(aminomethyl)thiazole. The yield of 2-chloro-5-(aminomethyl)thiazole was 93.3%, and the yield of bis{(2-chlorothiazol-5-yl)methyl}amine was 2.6%.

The solution containing 2-chloro-5-(aminomethyl)thiazole obtained was washed with 5.8 parts of an aqueous 14% sodium hydroxide solution, followed by addition of 17.5 parts of water and 9 parts of 35% hydrochloric acid to adjust to pH 4.9 to obtain 38.9 parts of an aqueous solution containing 2-chloro-5-(aminomethyl)thiazole hydrochloride. The content of 2-chloro-5-(aminomethyl)thiazole hydrochloride was 38.6% and the yield was 85.1%.

EXAMPLE 4

To a glass autoclave, 16.6 parts of 2-chloro-5-(chloromethyl)thiazole (content: 96.5%), 9.04 parts of paraformaldehyde (content: 95%) and 54.1 parts of a 10.5% ammonia solution in methanol were charged, and the mixture was reacted with stirring at an inner temperature of 70° C. for 3 hours. The maximum inner pressure (gauge pressure) during the reaction was 0.08 MPa. The reaction mixture containing 1,3,5-tris{(2-chlorothiazol-5-yl)methyl}-1,3,5-hexahydrotriazine obtained was transferred into a four-neck flask by washing the autoclave with 60 parts of methanol, and then concentrated under reduced pressure to obtain 40 parts of a concentrated residue. To the concentrated residue were added 73.2 parts of methanol and 32.8 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 42.8 parts of a concentrated residue. To the concentrated residue were added 11.4 parts of water, 49 parts of methyl isobutyl ketone and 60.9 parts of an aqueous 27% sodium hydroxide solution to adjust to pH 13, thereby subjecting the mixture to extraction treatment, and obtaining an organic layer and an aqueous layer. The aqueous layer was further extracted three times with methyl isobutyl ketone, and the methyl isobutyl ketone layers obtained were combined with the previously obtained organic layer to obtain a solution containing 2-chloro-5-(aminomethyl)thiazole. The yield of 2-chloro-5-(aminomethyl)thiazole was 91.2%, and the yield of bis{(2-chlorothiazol-5-yl)methyl}amine was 2.0%.

EXAMPLE 5

To a glass autoclave, 29 parts of 2-chloro-5-(chloromethyl)thiazole (content: 96.5%), 10.5 parts of paraformaldehyde (content: 95%) and 94.6 parts of a 9% ammonia solution in methanol were charged, and the mixture was reacted with stirring at an inner temperature of 70° C. for 3 hours. The maximum inner pressure (gauge pressure) during the reaction was 0.09 MPa. The reaction mixture containing 1,3,5-tris{(2-chlorothiazol-5-yl)methyl}-1,3,5-hexahydrotriazine obtained was transferred into four-neck flask by washing the autoclave with 60 parts of methanol, and then concentrated under reduced pressure to obtain 57.8 parts of a concentrated residue. To the concentrated residue were added 128 parts of methanol and 57.4 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 75.1 parts of a concentrated residue. To the concentrated residue were added 20 parts of water, 85.7 parts of methyl isobutyl ketone and 113.5 parts of an aqueous 27% sodium hydroxide solution to adjust to pH 13, thereby subjecting the mixture to extraction treatment, and obtaining an organic layer and an aqueous layer. The aqueous layer was further extracted with methyl isobutyl ketone, and the methyl isobutyl ketone layers obtained were combined with the previously obtained organic layer to obtain a solution containing 2-chloro-5-(aminomethyl)thiazole. The yield of 2-chloro-5-(aminomethyl)thiazole was 86.2%, and the yield of bis{(2-chlorothiazol-5-yl)methyl}amine was 4.3%.

EXAMPLE 6

To a glass autoclave, 10.6 parts of 2-chloro-5-(chloromethyl)thiazole (content: 95%), 2.3 parts of paraformaldehyde (content: 95%) and 30.5 parts of a 10% ammonia solution in methanol were charged, and the mixture was reacted with stirring at an inner temperature of 70° C. for 3 hours. The maximum inner pressure (gauge pressure) during the reaction was 0.10 MPa. The reaction mixture containing 1,3,5-tris{(2-chlorothiazol-5-yl)methyl}-1,3,5-hexahydrotriazine obtained was transferred into a four-neck flask by washing the autoclave with 30 parts of methanol, and then concentrated under reduced pressure to obtain 27.1 parts by weight of a concentrated residue. To the concentrated residue were added 45.8 parts of methanol and 11.8 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 35.8 parts of a concentrated residue. To the concentrated residue were added 30.6 parts of methyl isobutyl ketone and 24.5 parts of an aqueous 30% sodium hydroxide solution to adjust to pH 13, thereby subjecting the mixture to extraction treatment, and obtaining an organic layer and an aqueous layer. The aqueous layer was further extracted three times with methyl isobutyl ketone, and the methyl isobutyl ketone layers obtained were combined with the previously obtained organic layer to obtain a solution containing 2-chloro-5-(aminomethyl)thiazole. The yield of 2-chloro-5-(aminomethyl)thiazole was 80.1%, and the yield of bis{(2-chlorothiazol-5-yl)methyl}amine was 8.9%.

EXAMPLE 7

To a glass autoclave, 16.7 parts of 2-chloro-5-(chloromethyl)thiazole (content: 95.7%), 23.2 parts of formalin (content: 37%) and 30.9 parts of a 21% ammonia solution in methanol were charged, and the mixture was reacted with stirring at an inner temperature of 70° C. for 3 hours. The maximum inner pressure (gauge pressure) during the reaction was 0.05 MPa. The reaction mixture containing 1,3,5-tris{(2-chlorothiazol-5-yl)methyl}-1,3,5-hexahydrotriazine obtained was transferred into a four-neck flask by washing the autoclave with 60 parts of methanol, and then concentrated under reduced pressure to obtain 50.9 parts of a concentrated residue. To the concentrated residue were added 73.2 parts of methanol and 32.8 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 52.5 parts of a concentrated residue. To the concentrated residue were added 49 parts of methyl isobutyl ketone and 67.3 parts of an aqueous 27% sodium hydroxide solution to adjust to pH 13, thereby subjecting the mixture to extraction treatment, and obtaining an organic layer and an aqueous layer. The aqueous layer was further extracted three times with methyl isobutyl ketone, and the methyl isobutyl ketone layers obtained were combined with the previously obtained organic layer to obtain a solution containing 2-chloro-5-(aminomethyl)thiazole. The yield of 2-chloro-5-(aminomethyl)thiazole was 87.5%, and the yield of bis{(2-chlorothiazol-5-yl)methyl}amine was 2.2%.

EXAMPLE 8

To a glass autoclave, 29.3 parts of 2-chloro-5-(chloromethyl)thiazole (content: 95.7%), 15.8 parts of paraformaldehyde (content: 95% by weight) and 87.3 parts of a 13% ammonia solution in methanol were charged, and the mixture was reacted with stirring at an inner temperature of 70° C. for 3 hours. The maximum inner pressure (gauge pressure) during the reaction was 0.08 MPa. After completion of the reaction, the reaction mixture containing 1,3,5-tris{(2-chlorothiazol-5-yl)methyl}-1,3,5-hexahydrotriazine was cooled to an inner temperature of 5° C. to precipitate a solid, and the solid was collected by filtration. The collected solid was dried under reduced pressure to obtain 21.9 parts of 1,3,5-tris{(2-chlorothiazol-5-yl)methyl}-1,3,5-hexahydrotriazine.
MS(FD): m/z 480 at monoisotopic peak (isotopic pattern of Cl×3)
$^1$H-NMR (CDCl$_3$, 270 MHz, δ/ppm) 3.50(brs, 2H), 3.82(s, 2H), 7.33(s, 1H) $^{13}$C-NMR (CDCl$_3$, 68 MHz, δ/ppm) 48.85, 72.34, 138.73, 139.29, 151.71

The 1,3,5-tris{(2-chlorothiazol-5-yl)methyl}-1,3,5-hexahydrotriazine thus obtained was hydrolyzed with hydrochloric acid in methanol to obtain 2-chloro-5-(aminomethyl) thiazole. Yield: 65.9%. The yield of bis{(2-chlorothiazol-5-yl)methyl}amine was 0.5%.

EXAMPLE 9

To a stainless-steel autoclave, 15.5 parts of 2-chloro-5-(chloromethyl)thiazole (content: 96.5%), 8.7 parts of paraformaldehyde (content: 92%) and 24.4 parts of a 24% ammonia solution in methanol were charged, and the mixture was reacted with stirring at an inner temperature of 70° C. for 3 hours. The maximum inner pressure (gauge pressure) during the reaction was 0.02 MPa. The reaction mixture containing 1,3,5-tris{(2-chlorothiazol-5-yl)methyl}-1,3,5-hexahydrotriazine obtained was transferred into another flask by washing the autoclave with about 15 parts of methanol, and then concentrated under reduced pressure to obtain 45.2 parts by weight of a concentrated residue. To the concentrated residue was added methanol so as to make up the solution volume to 228 parts, and then added 32.5 parts of 35% hydrochloric acid, and the mixture was maintained with stirring at an inner temperature of 50° C. for 30 minutes. Then, the mixture was cooled to room temperature, and water was added thereto to obtain 260.2 parts of an aqueous solution containing 2-chloro-5-(aminomethyl)thiazole. The yield of 2-chloro-5-(aminomethyl)thiazole was 93.3%, and the yield of bis{(2-chlorothiazol-5-yl)methyl}amine was 2.0%.

COMPARATIVE EXAMPLE 1

To a stainless-steel autoclave, 15.7 parts of 2-chloro-5-(chloromethyl)thiazole (content: 95.7%) and 25.4 parts of a 24% ammonia solution in methanol were charged, and the mixture was reacted with stirring at an inner temperature of 70° C. for 3 hours. The maximum inner pressure (gauge pressure) during the reaction was 0.28 MPa. The reaction mixture obtained was transferred into another flask by washing the autoclave with about 15 parts of methanol, and then concentrated under reduced pressure to obtain 26.1 parts of a concentrated residue. To the concentrated residue was added methanol to obtain 228 parts of a solution containing 2-chloro-5-(aminomethyl)thiazole. The yield of 2-chloro-5-(aminomethyl)thiazole was 41.4%, and the yield of bis{(2-chlorothiazol-5-yl)methyl}amine was 24.5%.

EXAMPLE 10

To a glass autoclave, 29.3 parts of 2-chloro-5-(chloromethyl)thiazole (content: 95.7%), 15.8 parts of paraformaldehyde (content: 95%), 56.9 parts of a 20% ammonia solution in methanol and 43.9 parts of toluene were charged, and the mixture was reacted with stirring at an inner temperature of 70° C. for 5 hours. The maximum inner pressure (gauge pressure) during the reaction was 0.09 MPa. The reaction mixture containing 1,3,5-tris{(2-chlorothiazol-5-yl)methyl}-1,3,5-hexahydrotriazine obtained was transferred into a four-neck flask by washing the autoclave with 46 parts of methanol, and then concentrated under reduced pressure to obtain 162.4 parts of a concentrated residue. To the concentrated residue was added 23.6 parts of methanol and 57.4 parts of 35% hydrochloric acid, and the mixture was refluxed at an inner temperature of 60° C. for 1.5 hours. The mixture was cooled to an inner temperature of not higher than 40° C., and then concentrated under reduced pressure to obtain 74.3 parts of a concentrated residue. To the concentrated residue were added 20 parts of water, 85.7 parts of methyl isobutyl ketone and 108.2 parts of an aqueous 27% sodium hydroxide solution to adjust to pH 13, thereby subjecting the mixture to extraction treatment, and obtaining organic layer and an aqueous layer. The aqueous layer was further extracted three times with toluene, and the toluene layers obtained were combined with the previously obtained organic layer to obtain a solution containing 2-chloro-5-(aminomethyl)thiazole. The yield of 2-chloro-5-(aminomethyl)thiazole was 92.3%, and the yield of bis{(2-chlorothiazol-5-yl) methyl}amine was 2.2%.

Since the aqueous layer after extracted with toluene contained 2.5% of 2-chloro-5-(aminomethyl)thiazole as calculated from the yield, the reaction yield of 2-chloro-5-(aminomethyl)thiazole was 94.8%.

EXAMPLE 11

To a glass autoclave, 15.8 parts of paraformaldehyde (content: 95%) and 94.6 parts of a 12% ammonia solution in methanol were charged. To the mixture was added 29 parts of 2-chloro-5-(chloromethyl)thiazole (content: 96.6%) at room temperature, and the resultant mixture was reacted with stirring at an inner temperature of 40° C. for 3 hours, then at an inner temperature of 50° C. for 3 hours, and further at an inner temperature of 70° C. for 1 hour. The maximum inner pressure (gauge pressure) during the reaction was 0.09 MPa. The reaction mixture containing 1,3,5-tris{(2-chlorothiazol-5-yl) methyl}-1,3,5-hexahydrotriazine obtained was transferred into a four-neck flask by washing the autoclave with 60 parts of methanol, and then concentrated under reduced pressure to obtain 87.9 parts of a concentrated residue. To the concentrated residue was added 101 parts of water, and then the mixture was concentrated under reduced pressure to obtain 146.9 parts of a concentrated residue. To the concentrated residue was added 117 parts of toluene to subject the mixture to extraction treatment at an inner temperature of 75° C. to obtain 149 parts of a toluene layer and an aqueous layer. When the toluene layer was analyzed by HPLC, 1,3,5-tris{(2-chlorothiazol-5-yl)methyl}-1,3,5-hexahydrotriazine, 2-chloro-5-(aminomethyl)thiazole and bis{(2-chlorothiazol-5-yl)methyl}amine were contained in yields of 91.8%, 2.7% and 2.1%, respectively.

To 148.6 parts of the obtained toluene layer was added 21.5 parts of 35% hydrochloric acid with stirring, and then allowed to stand to separate into an oil layer and an aqueous layer. To the oil layer was added 1.2 parts of water to subject the mixture to extraction treatment, and the aqueous layer obtained was combined with the previously obtained aqueous layer. To the combined aqueous layer was added 39.5 parts of methanol, and the mixture was refluxed at an inner temperature of about 60° C. for 1.5 hours. The mixture was cooled to an inner temperature of not higher than 40° C., and then concentrated under reduced pressure to obtain 38.9 parts of a concentrated residue. To the concentrated residue were added 20 parts of water, 82.6 parts of toluene and 35 parts of an aqueous 27% sodium hydroxide solution to adjust to pH 13, thereby subjecting the mixture to extraction treatment, and obtaining an organic layer and an aqueous layer. The aqueous layer was further extracted three times with toluene, and the toluene layers obtained were combined with the previously obtained organic layer to obtain a solution containing 2-chloro-5-(aminomethyl)thiazole. The yield of 2-chloro-5-(aminomethyl)thiazole was 87.2%, and the yield of bis{(2-chlorothiazol-5-yl)methyl}amine was 1.9%.

INDUSTRIAL APPLICABILITY

According to the present invention, the thiazole compound of formula (3) which is useful as an intermediate for pharmaceuticals and agrochemicals can be prepared industrially advantageously with suppressing the formation of the by-product of formula (4).

What is claimed is:

1. A process for preparing a thiazole compound of formula (3):

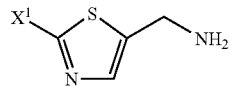
(3)

wherein $X^1$ represents a hydrogen atom or a halogen atom, which comprises the steps of:

reacting a compound of formula (1):

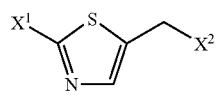
(1)

wherein $X^1$ is as defined above, and $X^2$ represents halogen atom, with ammonia and formaldehyde to obtain a hexahydrotriazine compound of formula (2):

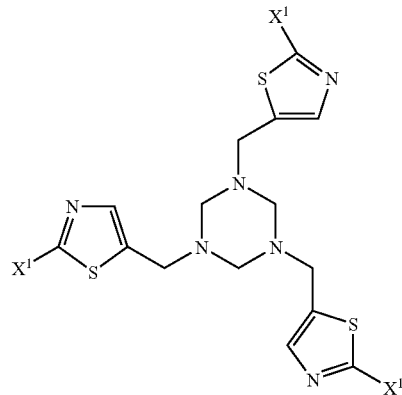
(2)

wherein $X^1$ is as defined above, and hydrolyzing the resulting hexahydrotriazine compound of formula (2).

2. The process according to claim 1, wherein formaldehyde is paraformaldehyde or formalin.

3. The process according to claim 1, wherein formaldehyde is used in the amount of 1 to 10 moles per mol of the compound of formula (1).

4. The process according to claim 1, wherein ammonia is used in the amount of 2 to 10 moles per mol of the compound of formula (1).

5. The process according to claim 1, wherein the hydrolysis is carried out by allowing to come into contact the hexahydrotriazine compound of formula (2) and an aqueous solution of an acid.

6. The process according to claim 5, wherein the hydrolysis is carried out in the presence of a lower alcohol compound.

7. A hexahydrotriazine compound of formula (2):

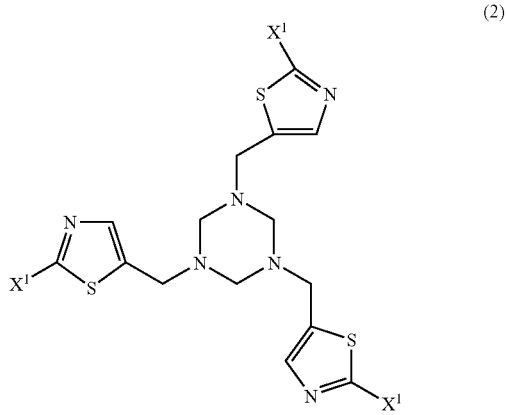
(2)

wherein $X^1$ represents a hydrogen atom or a halogen atom, or an acid addition salt thereof.

8. A process for preparing a hexahydrotriazine compound of formula (2):

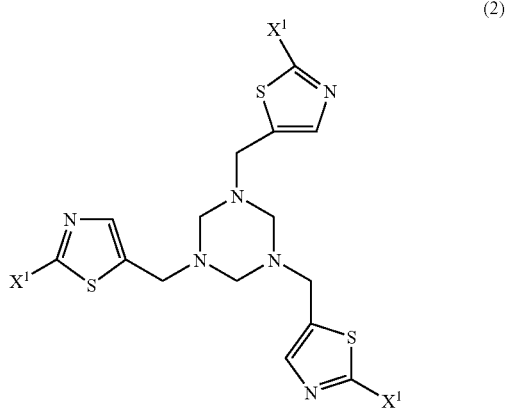
(2)

wherein $X^1$ represents a hydrogen atom or a halogen atom, which comprises reacting a compound of formula (1):

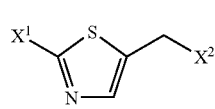
(1)

wherein $X^1$ is as defined above, and $X^2$ represents a halogen atom, with ammonia and formaldehyde.

9. The process according to claim 8, wherein formaldehyde is used in the amount of 1 to 10 moles per mol of the compound of formula (1).

10. The process according to claim 8, wherein ammonia is used in the amount of 2 to 10 moles per mol of the compound of formula (1).

11. A process for preparing a thiazole compound of formula (3):

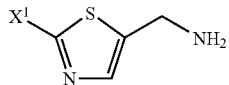
(3)

wherein $X^1$ represents a halogen atom, or a hydrogen atom, which comprises hydrolyzing a hexahydrotriazine compound of formula (2):

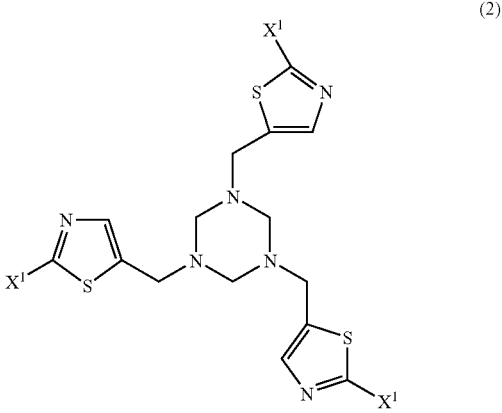
(2)

wherein $X^1$ is as defined above.

12. The process according to claim 11, wherein the hydrolysis is carried out by bringing the hexahydrotriazine compound of formula (2) into contact with an aqueous solution of an acid.

13. The process according to claim 12, wherein the hydrolysis is carried out in the presence of a lower alcohol compound.

* * * * *